United States Patent [19]
Stamey et al.

[11] Patent Number: 5,858,685
[45] Date of Patent: Jan. 12, 1999

[54] PROSTATE SPECIFIC ANTIGEN FROM BENIGN PROSTATIC HYPERPLASIA AND ITS USE IN DIAGNOSIS

[75] Inventors: Thomas A. Stamey, Portola Valley; Zuxiong Chen, Mountain View; John E. McNeal, Stanford, all of Calif.

[73] Assignee: The Board of Trustees of the Leland Stanford Junior University, Stanford, Calif.

[21] Appl. No.: 823,058

[22] Filed: Mar. 21, 1997

[51] Int. Cl.$^6$ ...................... G01N 33/573; G01N 33/531; G01N 33/574

[52] U.S. Cl. .................. 435/7.4; 435/7.23; 435/7.21; 435/212; 436/543; 530/388.26; 530/388.85; 530/350

[58] Field of Search .................. 435/7.21, 7.23, 435/7.4, 212; 436/543; 530/387.7, 387.9, 388.26, 388.85, 388.7, 350

[56] References Cited

U.S. PATENT DOCUMENTS 4,921,809  5/1990  Schiff et al. .......................... 436/531

OTHER PUBLICATIONS

Chen, et al., J. Virol., vol. 157, No. 6, pp. 2166–2170, Jun. 1997.

Joseph E. Osterling, "*Prostate–Specific Antigen: A Valuable Clinical Tool*", Oncology (Apr. 1991) 5:107–122.

Robert T. McCormack, Et Al., "*Molecular Forms of Prostate–Specific Antigen and the Human Kallikrein Gene Family: A New Era*", Urology (May 1995) 45:729–740.

Raffaele Baffa, Et Al., "*A Comparative Analysis of Prostate–Specific Antigen Gene Sequence In Benign and Malignant Prostate Tissue*", Urology (Feb. 1996) Urology 47: 795–800.

Marie–Blanche Tchetgen, Et Al., "*The Role of Prostate–Specific Antigen in the Evaluation of Benign Prostatic Hyperplasia*", Urology (May 1995) 22:333–344.

Tang J. Wang, Et Al., "*Dual Monoclonal Antibody Immunoassay for Free Prostate–Specific Antigen*", The Prostate (1996) 28:10–16.

T.A. Stamey, Et Al., "*Identity of PSA Purified from Seminal Fluid by Different Methods: Comparison by Amino Acid Analysis and Assigned Extinction Coefficients*", The Prostate (1995) 37:198–203.

Zuxiong Chen, Et Al., "*Purification and Characterization of Prostate–Specific Antigen (PSA) Complexed to Al–Antichymotrypsin: Potential Reference Material for International Standardization of PSA Immunoassays*", Clinical Chemistry (1995) 41:1273–1282.

Hans–Peter Schmid, Et Al., "*Observations on the Doubling Time of Prostate Cancer, the Use of Serial Prostate–Specific Antigen in Patients with Untreated Disease as a Measure of Increasing Cancer Volume*", Cancer (Mar. 15, 1993) 71:2031–2040.

Anthony F. Prestigiacomo, Et Al., "*A Comparison of the Free Fraction of Serum Prostate Specific Antigen In Men With Benign and Cancerous Prostates: The Best Case Scenario*", Urology (Aug. 1996) 156:350–354.

*Primary Examiner*—Toni R. Scheiner
*Attorney, Agent, or Firm*—Bret E. Field; Bozicevic & Reed LLP

[57] ABSTRACT

Benign prostatic hyperplasia-prostate specific antigen (BPH-PSA) and methods for its preparation are provided. Also provided are antibodies specific for BPH-PSA, and methods of their use in immunoassays for detecting the presence of BPH-PSA in a sample. The subject immunoassays find use in diagnosing the conditions associated with elevated serum PSA levels, such as prostate cancer and BPH.

21 Claims, 3 Drawing Sheets

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Ile  Val  Gly  Gly  Trp  Glu  Cys  Glu  Lys  His
1                   5                        10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

```
Val  Gly  Gly  Trp  Glu  Cys  Glu  Lys  His  Ser
1                   5                        10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
His  Pro  Glu  Asp  Thr  Gly  Gln  Val  Phe  Gln
1                   5                        10
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
Ser  Leu  Phe  His  Pro  Glu  Asp  Thr  Gly  Gln
1                   5                        10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( x i ) SEQUENCE DESCRIPTION: SEQ ID NO:5:

```
Lys  Leu  Gln  Cys  Val  Asp  Leu  His  Val  Ile
1                   5                        10
```

( 2 ) INFORMATION FOR SEQ ID NO:6:

( i ) SEQUENCE CHARACTERISTICS:

(A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Leu Gln Cys Val Asp Leu His Val Ile
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Ile Val Gly Gly Trp
1               5

(2) INFORMATION FOR SEQ ID NO:8:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Val Gly Gly Trp
1

PROSTATE SPECIFIC ANTIGEN FROM BENIGN PROSTATIC HYPERPLASIA AND ITS USE IN DIAGNOSIS

INTRODUCTION

1. Technical Field

The field of this invention is prostate cancer and benign prostatic hyperplasia (BPH).

2. Background of the Invention

Prostate cancer is a type of cancer which solely afflicts the male population. Currently, prostate cancer accounts for a significant proportion of all the newly diagnosed cancers in males in the United States; next to lung cancer, it is the most common cause of cancer deaths in males. Furthermore, the occurrence of prostate cancer is predicted to increase substantially in the United States and other regions of the world characterized by aging populations. BPH affects 20–30% of all males in the United States, and it is the major cause of obstructive urinary symptoms. About 500,000 men in the United States are treated each year for urinary tract obstruction.

Prostate neoplasms are almost always adenocarcinomas which, if treated sufficiently early in the progression of the disease, have a substantial cure rate. Therefore, while still controversial, much emphasis in current prostate cancer management is placed on methods of screening patients in an effort to detect the presence of prostate cancer at an early stage of the disease. Screening methods currently employed include digital rectal examination, transrectal ultrasonography (TRUS) and serum prostate specific antigen (PSA) level determination, in which the serum PSA level is used as marker for the presence of prostate cancer.

PSA is a serine protease with chymotrypsin-like enzymatic activity. The mature from of PSA has isoleucine as the N-terminus, and 237 amino acid residues with a molecular mass of 28,400. PSA is found in serum in two forms, a free form and a form complexed with $\alpha_1$-antichymotrypsin (PCT-ACT).

Most FDA approved immunoassays which measure the PSA serum level look at the total PSA serum level, i.e. the amount of PSA in both the free and complexed form. While such assays have proved useful in the diagnosis of prostate cancer, the results are not always reliable. This unreliability arises, at least in part, from the fact that PSA is not specific for prostate cancer, as it is detected in both normal and cancerous prostate tissues, and especially in men with benign prostatic hyperplasia (BPH) tissue. Thus, the diagnostic utility of PSA is limited by the difficulty in distinguishing elevated levels of serum PSA due to BPH from elevated PSA levels resulting from the presence of prostate cancer, especially when serum PSA is >4 ng/ml.

In order to improve the specificity of assays in which serum PSA is used as a marker, several different approaches have been taken. Such approaches include determining PSA velocity, PSA density, providing for age adjustment, establishing a neural network based on multiple input vectors, and the like. One approach which appears to be promising is to look at not just the total serum PSA level, but the ratio of different molecular forms of PSA, i.e. free PSA to total PSA. See Froschermaier et al., Urology (1996) 47:525–528.

Although such approaches have increased the proportion of successful diagnoses which are made using PSA as a marker, there remains a need for yet further improvement in such methods. Specifically, the ranges of the different molecular forms of serum PSA which are associated with BPH and prostate cancer overlap substantially. Furthermore, the quantitation methods employed to quantify the amounts of the different forms of serum PSA can lead to confounded results.

Accordingly, there is interest in the development of yet further methods of using PSA as a marker in the diagnosis of prostate cancer. Such methods would ideally be able to reliably distinguish between elevated serum PSA levels resulting from BPH-PSA and prostate cancer.

Relevant Literature

McCormack et al., Urology (1995) 45:729–740 provides a review of the different molecular forms of PSA. Baffa et al., Urology (1996) 47:795–800 reports on the results of a comparative analysis of the PSA gene sequence of benign and malignant prostate tissue. The use of PSA as a screening tool for the early diagnosis of prostate cancer is reviewed in Oesterling, Oncology (1991) 5:107–122. The efficacy of different methods of distinguishing BPH from prostate cancer where PSA is used as a marker is reviewed in Tchetgen and Oesterling, Urol. Clin. North Am. (1995) 22:333–344. Wang et al., Prostate (1996) 28:10–16 describes an immunoassay for f-PSA and PSA-ACT complex.

Other references of interest include: Stamey et al., Prostate (1995) 27:198–203; Chen et al., Clin.Chem. (1995) 41:1273–1282; Schmid et al., Cancer 91993) 71:2031–2040; Prestigiacomo et al., J. Urol. (1996) 156: 350–354.

SUMMARY OF THE INVENTION

Benign Prostatic Hyperplasia-Prostate Specific Antigen (BPH-PSA)and methods for its collection and preparation are provided. BPH-PSA is collected by a novel method in which multiple incisions are made into freshly enucleated BPH harvested during open retropubic surgery. BPH-PSA fluid, which exudes from each incision, is collected with a needle and syringe at the bottom of each incised crevice. Also provided are antibodies specific for BPH-PSA and methods for their use in detecting the presence of BPH-PSA in sample. The subject methods find use in the diagnosis of conditions in which serum PSA is used as a marker, such as prostate cancer and BPH.

DESCRIPTION OF THE SPECIFIC EMBODIMENTS

Benign Prostatic Hyperplasia-Prostate Specific Antigen (BPH-PSA) and methods for its extraction, purification and concentration are provided. Also provided are antibodies specific for BPH-PSA and methods of their use in assays capable of detecting the presence of BPH-PSA in a sample. The subject immunoassay methods find use in the diagnosis of conditions in which serum PSA is used as a marker, such as prostate cancer and BPH. In further describing the subject invention, BPH-PSA will first be described in greater detail, followed by a discussion of the preparation of antibodies specific for the subject BPH-PSA and a description of their use in immunoassays.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

The BPH-PSA is processed in some manner so as to be present in a non-naturally occurring environment, where non-naturally occurring environment includes a variety of different compositions, e.g. substantially pure BPH-PSA, purified preparations of BPH-PSA, preparations that are concentrated or enriched with respect to BPH-PSA, and the like. The BPH-PSA of the subject invention may be present in substantially pure form, or as a component in a preparation which is at least partially purified, concentrated and/or enriched with respect to BPH-PSA as compared to naturally occurring compositions in which BPH-PSA is present, e.g. BPH nodule fluid. Where BPH-PSA is present in substantially pure form, it will make up at least about 90%, usually at least about 95% and more usually at least about 99% by wt. of the composition in which it is present. In preparations that are at least partially purified, concentrated and/or enriched with respect to BPH-PSA, what is meant is that the specific immunoreactivity of BPH-PSA in the preparation will be at least about 5 times, usually at least about 10 times and more usually at least about 15 times greater the specific immunoreactivity of BPH-PSA in BPH nodule fluid, where the specific activity will generally be at least about 0.25 mg/$A_{280}$, usually at least about 0.50 mg/$A_{280}$.

The BPH-PSA of the subject invention migrates as a single band on SDS-PAGE under non-reducing conditions with a molecular weight of about 30 kDa. Under reducing conditions, BPH-PSA migrates on SDS-PAGE as multiple bands ranging in molecular weight from about 8 kDa to about 30 kDa.

The enzymatic activity of BPH-PSA differs substantially from that of seminal fluid PSA (SF-PSA). When enzymatic activity is measured indirectly by incubating BPH-PSA with female serum and evaluating immunoreactivity as described in J. Urol. (1996) 156:1357–1363, the subject BPH-PSA is only about 20% enzymatically active, compared with SF-PSA which is about 50% enzymatically active under the same conditions. Furthermore, using the assay described by Christiansen et al, Eur. J. Biochem. (1990) 194:755–763, while the trypsin like activity of BPH-PSA is substantially the same as the trypsin like activity of SF-PSA as measured by contact with the synthetic substrate S2303, the chymotrypsin like activity of BPH-PSA is substantially less than the chymotrypsin like activity of SF-PSA, where by substantially less than is meant that less than about 20%, usually less than about 17% of the chymotrypsin like activity of SF-PSA, as measured by contact with the synthetic substrate S2586.

Standard N-terminal amino acid analysis of the subject BPH-PSA demonstrates that at least a portion of any given population of BPH-PSA molecules differs from SF-PSA in terminating in valine instead of isoleucine, i.e. two N-terminal amino acid sequences are observed: IVGGW and VGGW. The subject BPH-PSA is further characterized by N-terminal amino acid sequence analysis as having multiple internal cleavage sites. Specifically, the following internal cleavage sites are observed: His54-Ser55; Phe-57-His58; Lys 145-Lys 146; and Lys 146-Leu 147.

In preparing the subject BPH-PSA, it is critical to start with a naturally occurring source of BPH-PSA, since BPH-PSA is modified post-translationally in its native environment. Preferably, the source of BPH-PSA employed is BPH-PSA nodule fluid, which may be obtained using any convenient means. One particularly preferred means for obtaining BPH nodule fluid is to obtain BPH nodules from human males having benign prostatic hyperplasia, and extracting BPH-PSA comprising fluid from the nodules by harvesting fluid from the nodules by piercing the nodules and collecting fluid that seeps out of the nodules.

The BPH-PSA may be purified, concentrated and/or enriched from the naturally occurring source using any convenient methodology, where a variety of methodologies for protein purification are known in the art. See Guide to Protein Purification (Murray P. Deutscher ed., Harcourt Brace & Co.)(1990). Generally, the purification procedure employed will comprise one or more steps which result in the separation of BPH-PSA from at least a portion of the other components of the naturally occurring source from which it is to be purified. Viewed another way, the purification will be any method in which one or more components of the initial sample are separated from the sample so as to enrich the remaining sample with respect to BPH-PSA, i.e. increase the concentration of BPH-PSA in the remaining sample. The purification conditions should be mild so as to avoid denaturation of the BPH-PSA. To avoid autocleavage of the BPH-PSA, a buffer pH ranging from about 5.0 to 6.0, usually from about 5.4 to 5.8 is preferred.

One preferred method of purifying BPH-PSA is a two step chromatographic procedure. Prior to this procedure, the naturally occurring fluid source of BPH-PSA, e.g. BPH nodule fluid, may be clarified to remove any particulate matter from the fluid, such as by centrifugation, where centrifugation will usually be at least about 0.5 hr, more usually at least about 0.75 hr, more usually at least about 1 hr, at speeds ranging from about 20,000 to 40,000 rpm, more usually at about 30,000 rpm. In the two step chromatographic procedure, the clarified supernatant is first subjected to size exclusion, e.g. gel chromatography. Matrices suitable for use in this first step will be those matrices designed for the separation of protein mixtures comprising differently sized proteins ranging in size from about 5 to 2000 kDa, usually 10 to 800 kDa, where such matrices include BioGel A-0.5 m, BioGel A-1.5 m, Sephacryl S-200, Ultragel AcA 22, and the like, with Sephacryl S200 being preferred. The flow rate of the buffer through the column will generally range from about 0.20 to 0.30 ml/min, with a flow rate of about 0.25 ml/min being preferred. Elution fractions are collected and assayed for PSA activity using any convenient assay, such as Tosoh-AIA®-600 assay, and the like. Fractions testing positive for PSA activity are then separated from any assay reagents, e.g. by dialysis, and then subjected to a second ion exchange chromatographic procedure. Any suitable ion exchange material capable of providing for weak cationic exchange may be employed, where suitable materials include CM-cellulose, CM-Sephadex, and the like. Following column preparation, the fractions from the previous procedure will be loaded onto the column and the column washed a sufficient number of times, e.g. three times, to permit any unbound sample components to pass through. For elution of the protein, a linear salt gradient, e.g. sodium chloride from 0.0 to 1.0M, is passed through the column and the resultant fractions assayed for the presence of BPH-PSA. The fractions comprising BPH-PSA may be subjected to further purification, such as additional column chromatography, gel electrophoresis, and the like.

Antibodies that specifically bind to the subject BPH-PSA can be prepared using a variety of convenient methods known to those of skill in the art. See Guide to Protein Purification, supra, as well as Antibodies, A Laboratory Manual (Harlow & Lane eds., Cold Spring Harbor Press) (1988). The antibodies may be polyclonal or monoclonal antibodies depending on the nature of the intended use, as long as they are specific for BPH-PSA and do not cross-react with SF-PSA or the PSA-ACT complex. Depending on the desired use of the antibodies, in some cases monoclonal antibodies will be preferred, where representative antibodies include 3F12, 3H1, 3H4, 5F3, 6C5, 7D1, 7E8, 1C7, 4B5, 4C4, 5B5, 7E12 and 7H9.

For preparation of polyclonal antibodies, the first step is immunization of the host animal with BPH-PSA, where the BPH-PSA will preferably be in substantially pure form, comprising less than about 1% contaminant. The immunogen may comprise complete BPH-PSA, fragments or derivatives thereof. To increase the immune response of the host animal, the BPH-PSA may be combined with an adjuvant, where suitable adjuvants include alum, dextran, sulfate, large polymeric anions, oil & water emulsions, e.g. Freund's adjuvant, Freund's complete adjuvant, and the like. The BPH-PSA may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The BPH-PSA is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

As with the preparation of polyclonal antibodies, the first step in preparing monoclonal antibodies specific for BPH-PSA is to immunize a suitable host, where suitable hosts include rats, hamsters, mice and the like, and are preferably mice. The BPH-PSA immunogen, which as above may be the entire BPH-PSA protein or a fragment or derivative thereof, is administered to the host in any convenient manner, where such methods include: subcutaneous injection with adjuvants, nitrocellulose implants comprising BPH-PSA, intrasplenic injections, and the like, where the immunization protocol may be modulated to obtain a desired type of antibody, e.g. IgG or IgM, where such methods are known in the art. Following immunization, plasma cells are harvested from the immunized host, where sources of plasma cells include the spleen, lymph nodes and the like, with the spleen being preferred. The plasma cells are then immortalized with myeloma cells to produce hybridoma cells. A variety of myeloma cell lines are available, where the myeloma cell line will preferably be HGPRT negative, incapable of producing or secreting its own antibodies, and growth stable, where specific cell lines of interest include p3U1, SP 2/0 Ag14, P3×63Ag8.653 (Dr. Greenberg, V. A. Hospital) and the like. The plasma and myeloma cells are fused by combining the cells in a fusion medium usually in a ratio of about 10 plasma cells to 1 myeloma cell, where suitable fusion mediums include a fusion agent, e.g. PEG 1000, and the like. Following fusion, the fused cells will be selected, e.g by growing on HAT medium. Representative hybridomas according to the subject invention include those hybridomas that secrete one of the following monoclonal antibodies: 3F12, 3H1, 3H4, SF3, 6C5, 7D1, 7E8, 1C7, 4B5, 4C4, 5B5, 7E12 and 7H9. Following hybridoma cell production, culture supernatant from individual hybridomas is screened for reactivity with BPH-PSA using standard techniques, where such screening techniques include ELISA, dot blot immunoassays and the like. The antibody may be purified from the supernatants or ascites fluid by conventional techniques, e.g. affinity chromatography BPH-PSA bound to an insoluble support, protein A sepharose and the like.

The above prepared antibodies may be modified in a number of different ways to optimize their utility for use in a particular immunoassay. For example, antibody fragments, such as Fv, F(ab')$_2$ and Fab may be prepared by cleavage of the intact protein, e.g. by protease or chemical cleavage. The antibodies, fragments or derivatives thereof may also be labeled in order to facilitate detection. A variety of protein labeling schemes are known in the art and may be employed, the particular scheme and label chosen being the one most convenient for the intended use of the antibody, e.g. immunoassay. Examples of labels include labels that permit both the direct and indirect measurement of the presence of the antibody. Examples of labels that permit direct measurement of the antibody include radiolabels, such as $^3$H or $^{125}$I, fluorescers, dyes, beads, chemilumninescers, colloidal particles, and the like. Examples of labels which permit indirect measurement of the presence of the antibody include enzymes where a substrate may provided for a colored or fluorescent product. For example, the antibodies may be labeled with a covalently bound enzyme capable of providing a detectable product signal after addition of suitable substrate. Instead of covalently binding the enzyme to the antibody, the antibody may be modified to comprise a first member of specific binding pair which specifically binds with a second member of the specific binding pair that in conjugated to the enzyme, e.g the antibody may be covalently bound to biotin and the enzyme conjugate to streptavidin. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

The subject antibodies find use in immunoassays that are capable of providing for the detection of BPH-PSA in a sample. In such assays, the sample suspected of comprising BPH-PSA will usually be serum from a human host suspected of having BPH or prostate cancer. The serum may be pretreated prior to assay, as may be desirable depending on the particular assay to be performed.

A number of different immunoassay formats are known in the art and may be employed in detecting the presence of BPH-PSA with the subject antibodies in a sample, where such immunoassays include those assays employing a single type of antibody specific for BPH-PSA and those assays employing two different types of antibody which are capable of concomitantly recognizing and specifically binding to different epitopes of the BPH-PSA.

Immunoassays in which only a single type of antibody specific for BPH-PSA include Western blots on protein gels or protein spots on filters, where the antibody is labeled as described above, as is known in the art. Other immunoassays include those based on a competitive formats, as are known in the art. One such format would be where a solid support is coated with BPH-PSA. Labeled BPH-PSA antibody is then combined with a sample suspected of comprising BPH-PSA to produce a reaction mixture which, following sufficient incubation time for binding complexes to form, is contacted with the solid phase bound BPH-PSA. The amount of labeled antibody which binds to the solid phase will be proportional to the amount of BPH-PSA in the sample, and the presence of BPH-PSA may therefore be detected. Other competitive formats that may be employed include those where the sample suspected of comprising BPH-PSA is combined with a known amount of labeled BPH-PSA and then contacted with a solid support coated with antibody specific for BPH-PSA. Such assay formats are known in the art and further described in both Guide to Protein Purification, supra, and Antibodies, A Laboratory Manual, supra.

Where one has two different types of antibodies capable of concomitantly recognizing and binding to distinct epitopes of BPH-PSA, the opportunity exists to perform sandwich-format assays. A sandwich assay is performed by initially attaching a first of the two types of antibodies to an insoluble surface or support. This first antibody may be bound to the surface by any convenient means, depending upon the nature of the surface, either directly or through specific antibodies. The particular manner of binding is not crucial so long as it is compatible with the reagents and overall methods of the invention. They may be bound to the plates covalently or non-covalently, preferably non-covalently.

The insoluble supports may be any compositions to which antibodies or fragments thereof can be bound, which is readily separated from soluble material, and which is otherwise compatible with the overall method of measuring BPH-PSA. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support i.e. those not occupied by the first antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof are then added to separately assayable supports (for example, separate wells of a microtiter plate) containing support-bound allergen. Preferably, a series of standards, containing known concentrations of BPH-PSA is assayed in parallel with the samples or aliquots thereof to serve as controls.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for BPH-PSA molecules to bind the insoluble first antibody. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7–8, is used as a wash medium. From one to six washes may be employed, with sufficient volume to thoroughly wash non-specifically bound proteins present in the sample.

After washing, a solution containing the second BPH-PSA specific antibody is applied. The second antibody may be labeled, as described above, to facilitate direct, or indirect detection and/or quantification of binding. Examples of labels which permit direct measurement of immunocomplexes include radiolabels, such as $^3$H or $^{125}$I, fluorescers, dyes, beads, chemilumninescers, colloidal particles, and the like. Examples of labels which permit indirect measurement of binding include enzymes where the substrate may provide for a colored or fluorescent product. In a preferred embodiment, the second antibody is labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the antibody may be unlabeled. In this case, a labeled second receptor-specific compound is employed which binds to the second antibody. Such a second receptor-specific compound can be labeled in any of the above manners. It is possible to select such compounds such that multiple compounds bind each molecule of bound second receptor. Examples of second antibody/second receptor-specific molecule pairs include antibody/anti-antibody and avidin (or streptavidin)/biotin. Since the resultant signal is thus amplified, this technique may be advantageous where only a small amount of BPH-PSA is present. An example is the use of a labeled antibody specific to the second antibody.

The volume, composition and concentration of second antibody solution provides for measurable binding to the BPH-PSA already bound to the first antibody. Generally, the same volume as that of the sample is used: from about 0.001 to 1 ml is sufficient, usually about 0.1 ml sufficing. The concentration will generally be sufficient to saturate all BPH-PSA potentially bound to first antibody. The concentration generally will be about 0.1 to 50 $\mu$g/ml, preferably about 1 $\mu$g/ml. The solution containing the second antibody is generally buffered in the range of about pH 6.5–9.5. The solution may also contain an innocuous protein as previously described. The incubation time should be sufficient for the labeled ligand to bind available molecules. Generally, from about 0.1 to 3 hr is sufficient, usually 1 hr sufficing.

After the second antibody has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

Kits for providing the subject immunoassays are also provided. Generally, such kits comprise at least antibody specific for BPH-PSA and any reagents necessary for the detection of antibody-BPH-PSA binding complexes. The kits may further comprise other components of the immunoassay, such as solid support, solutions and the like.

It is particularly convenient in a clinical setting to perform the immunoassay in a self-contained apparatus, and such devices are provided by the subject invention. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it the first antibody, and second labeled antibody combined with the assayed sample and the sandwich assay performed as above.

The subject immunoassays find use in the diagnosis of both BPH-PSA and prostate cancer. By identifying the presence of BPH-PSA, one can attribute elevated total PSA levels to the presence of BPH-PSA as opposed to prostate cancer, and therefore obtain more reliable diagnoses of one or both of these conditions.

The following examples are offered by way of illustration and not by way of limitation. The following examples are put forth so as to provide those of ordinary skill in the art with a complete disclosure and description of how to make and use the subject sets of fluorescent labels.

EXPERIMENTAL

I. BPH-PSA Purification and Characterization

A. Materials

PSA was purified from human seminal plasma as described previously (Sensabaugh & Blake, J. Urol. (1990) 144:1523–1526) with modification. ACT was purchased from Athens Research Technology (Athens, Ga.). Two monoclonal antibodies to PSA, 2E9 and F5, were obtained as a gift from Dr. Hans Lilja (Malmö, Sweden) and Ciba-Corning Diagnostics (East Walpole, Mass.), respectively. Sephacryl S-200 was purchased from Pharmacia (Uppsala, Sweden). CM-cellulose, anti-mouse IgG-alkaline phosphatase conjugate (from goat), nitroblue tetrazolium (NBT), and 5-bromo-4-chloro-3-indolyl phosphate (BCIT) were from Sigma Chemical Co. (St. Louis, Mo.). Nitrocellulose membrane was obtained from Schleicher & Schuell (Keene, N.H.). Polyvinylidene difluoride (PVDF) membrane, molecular mass calibration proteins, and other reagents for gel electrophoresis were from Bio-Rad Labs (Hercules, Calif.). Synthetic substrates, Meo-Suc-Arg-Pro-Tyr-PNA-HCL (S-2586) (3-Carbomethoxypropiony-Larginyl-proyl-L-tyrosine-P-nitroaniline hydrochloride) and H-D-Pro Phe-Ary-pNA-2HCl (S-2302) (H-D-prolyl-Phenylalanyl-L Arginin-p-nitroanilid-dilydro-chloride) were purchased from Chromogenix (Franklin, Ohio). Female serums were collected from healthy volunteers in the Department of Urology. Tosoh AIA®-600 immunoassay reagents for PSA were from Tosoh (Foster City, Calif.).

B. Methods

Figure 1:
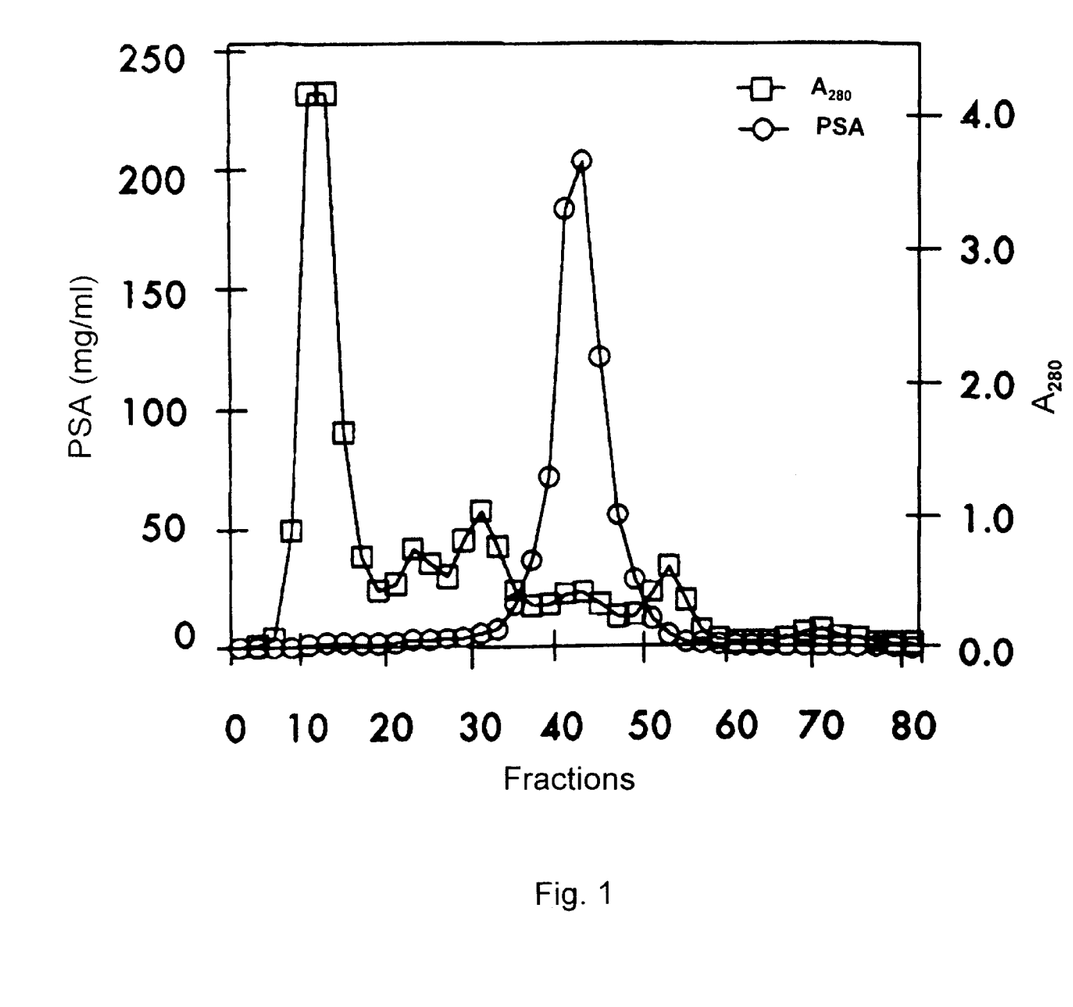
FIG. 1 is a graphical representation of the results of Sephacryl S-200 gel filtration chromatography of BPH nodule fluids.
Figure 2:
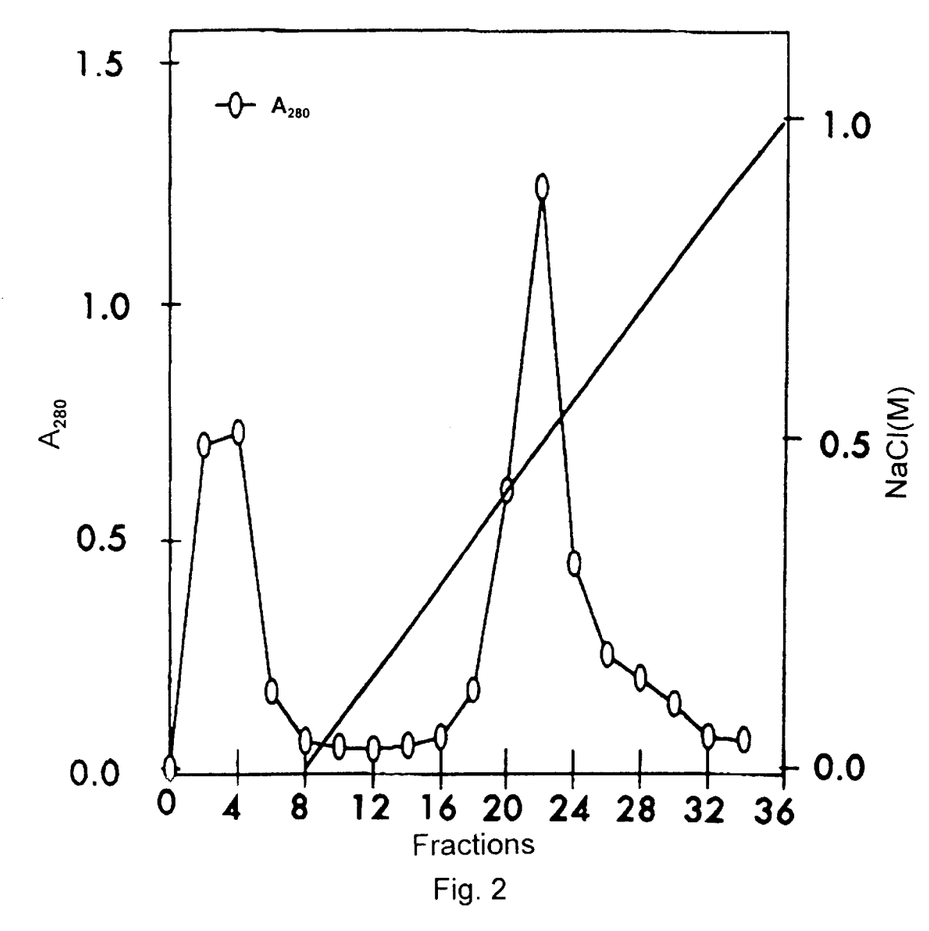
FIG. 2 is a graphical representation of the results of CM-cellulose chromatography of BPH nodule fluids.

1. Purification of PSA from BPH nodule fluids: BPH nodule fluids were collected and combined from BPH nodules in 2 patients undergoing simple retropubic enucleation; briefly, the BPH fluid was collected by plunging a #22 surgical knife blade into the enucleated nodules and collecting the fluid at the surface with a pipette, needle or blunt end of a 3 mL syringe. The fluid was centrifuged at 30,000 rpm for 60 min, and the supernatant (2 mL) was applied to a Sephacryl S-200 column (2.5×160 cm) equilibrated with 20 mM sodium acetate buffer containing 0.15M NaCl, pH 5.6, at a flow rate of 0.25 mL/min. The column was washed with the same buffer until the absorbance at 280 nm ($A_{280}$) reached the baseline, then 1.5 mL fractions were collected. Six protein peaks were separated by measuring absorbance at 280 nm (FIG. 1). Only Peak 4 contained PSA immunoreactivity by the Tosoh AIA®-600 assay which was then dialyzed over night with 20 mM sodium acetate buffer, pH 5.6, concentrated to 1.5 mL, and applied to a CM-cellulose column (0.8×8.5 cm). This second column was equilibrated with 20 mM sodium acetate buffer, pH 5.6, and washed with 3 times the column bed volume using the same buffer at a flow rate of 0.15 mL/min. The column was then eluted with 36 mL of a linear gradient of sodium chloride from 0 to 1M in the same buffer. A single protein peak, PSA, eluted at 0.25M of salt (FIG. 2). Fractions 18 to 26 were combined for characterization.

Electrophoresis: Sodium dodecyl sulfate-polyacrylamide gel electrophoresis (SDS-PAGE) was performed by the method of Laemmli, Nature (1970) 227:685, with modification as described in Schagger and von Jagow, Anal. Biochem. (1987) 166:368–379; the spacing gel portion was omitted so that the vertical slab gel contained only stacking gel. Western Blot was performed according to the method of Turner, J. Immunol. Methods (1983) 63:1–6.

Enzyme assay: The enzymatic activity of PSA was determined by hydrolyzing synthetic substrates, S-2586 and S-2302, as suggested by Christensson et al. Eur. J. Biochem. (1990) 194:755–763. All enzyme assays were done at 37° C. Hydrolysis was terminated by adding glacial acetic acid, and the absorbance at 405 nm was measured by spectrophotometer as described in Svendsen et al., Thromb. Res. (1972) 1:267–278.

Amino Acid sequence: PSA and its degraded fragments purified from BPH nodule fluid were prepared for sequencing, following SDS-PAGE and blotting onto a PVDF membrane, as described by Matsudaira, J. Biol.Chem (1987) 262:10035–10038. The bands of protein were subjected to at least 10 cycles of Edman degradation and PTH-amino acid detection performed at the University of Georgia with Procise 494 gas-phase sequenator using the program designed by the manufacturer.

Immunoassay: The immunoreactivity of PSA was determined by Tosoh AIA®-600 assay according to the manufacturer's instruction.

C. Results

TABLE 1

Purification of PSA from BPH nodule fluid

| step | total $A_{280}$ | PSA (mg) | yield (%) | sp. act.[1] (mg/$A_{280}$) | purification |
|---|---|---|---|---|---|
| nod. flu.[2] | 92.3 | 3.7 | 100 | 0.04 | 1 |
| S-200[3] | 8.83 | 2.68 | 72.4 | 0.30 | 7.5 |
| CM[4] | 3.51 | 2.39 | 64.6 | 0.68 | 17 | sp. act.[1]: specific immunoreactivity.
nod. flu.[2]: BPH nodule fluid.
S-200[3]: Sephacryl S-200 column chromatography.
CM[4]: CM-cellulose column chromatography.

Sephacryl S-200 gel filtration chromatography served as a useful starting procedure for purification because it produced about an 8-fold purification. As shown in FIG. 1, measuring the absorbance at 280 nm produced six separate peaks with only Peak 4 containing PSA immunoreactivity. The Peak 4 fraction was further purified on CM-cellulose column; as shown in FIG. 2, the contaminating protein had no PSA immunoreactivity and passed through the column, whereas BPH nodule fluid PSA was bound to the CM-cellulose column. It was then eluted at 0.25M sodium chloride by a linear gradient of salt, which provided an additional 2-fold purification (Table 1). for comparison, the identical procedure was used for purifying PSA from seminal plasma and similar results were obtained (data not shown).

Figure 3:
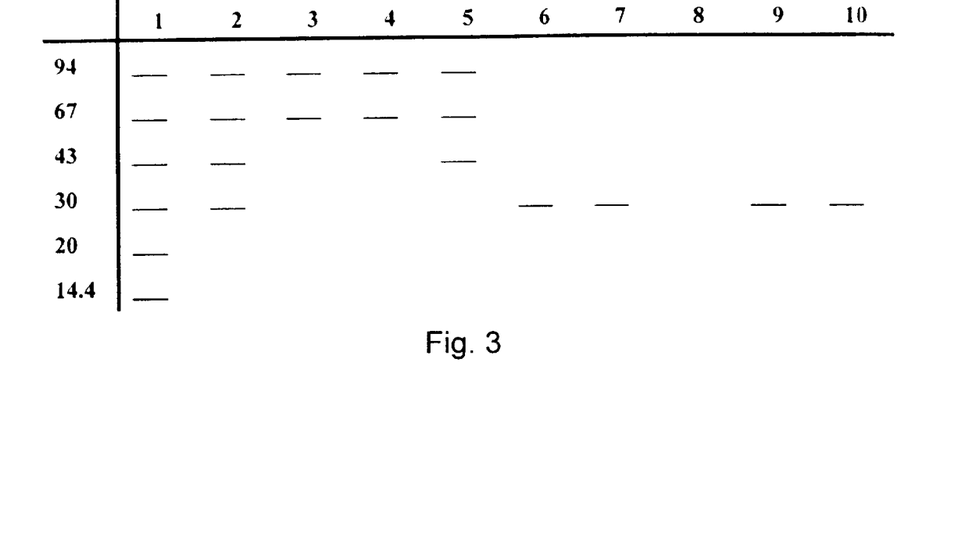
FIG. 3 is a representation of an SDS-PAGE which describes purification of BPH-PSA.

Purity: PSA purified from BPH nodule fluid had a single band on SDS-PAGE and the results are shown in the representation of FIG. 3. SDS-PAGE was performed as described in the methods. All samples were boiled with SDS sample buffer for 3 min. The protein bands were visualized by staining with Coomassie Brilliant Blue R250. Lane 1, molecular mass markers (phosphorylase B, 94 kDa; BSA, 67 kDa; ovalbumin, 43 kDa; carbonic anhydrase, 30 kDa; soybean trypsin inhibitor, 20 kDa; α-lactalbumin, 14.4 kDa); Lane 2, BPH nodule fluid; Lane 3 through Lane 8, Peaks 1, 2, 3, 4, 5, 6 of Sephacryl S-200 column, respectively; Lane 9, purified BPH-PSA; Lane 10, purified seminal fluid PSA.

As shown in FIG. 3, Lane 9, under nonreducing conditions, a single band was observed when stained with Coomassie Brilliant Blue.

Figure 4:
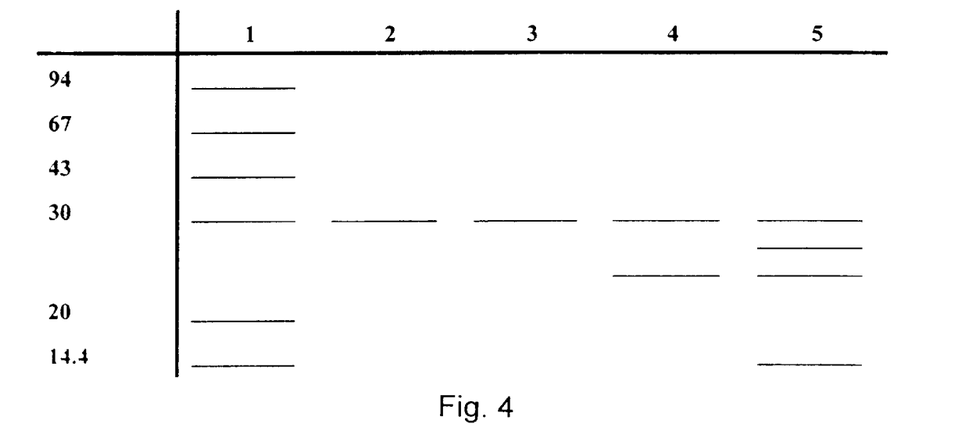
FIG. 4 is a representation of an SDS-PAGE showing the difference between seminal fluid PSA (SF-PSA) and BPH-PSA under reducing conditions.

SDS-PAGE was also performed under reducing conditions and the results are provided in the representation of FIG. 4. SDS Gel electrophoresis was performed as described in the Methods, above. All samples were boiled for 3 min. Samples in Lanes 1 and 2 were boiled with SDS sample buffer only, whereas samples in Lanes 3 and 4 were boiled with SDS and β-mercatoethanol. Lane 1, molecular mass markers (same as in FIG. 3); Lanes 2 and 4, seminal fluid PSA; Lanes 3 and 5, BPH nodule fluid PSA. However, under reducing conditions, BPH-PSA showed several bands on the SDS-PAGE varying from 30 kDa to 8 kDa (FIG. 4, Lane 5). These bands had amino-terminal sequences identical to that of seminal fluid PSA, indicating that they represented fragments from the nicked form of BPH-PSA. If Lane 4 is compared to Lane 5 in FIG. 4, more than half of BPH-PSA is in the nicked form, whereas the majority of seminal fluid PSA is in the intact form.

Enzyme activity: The enzymatic activity of BPH-PSA is different from that of seminal fluid PSA. Indirect evaluation of this activity was carried out by calculating the signal loss after PSA was incubated with female serums. The results are shown in Table 2.

TABLE 2

Comparison of immunoreactivity-loss of BPH-PSA and seminal fluid PSA (SF-PSA) in female serum

|  | pre-incubation (ng/mL) | post-incubation (ng/mL) | loss |
|---|---|---|---|
| BPH-PSA | 10.27 (100%) | 7.72 (75.2%) | 24.8% |
|  | 4.85 (100%) | 3.78 (77.9%) | 22.1% |
| SF-PSA | 19.09 (100%) | 9.29 (48.7%) | 51.3% |
|  | 9.53 (100%) | 4.37 (45.9%) | 54.1% |

Purified BPH nodule fluid PSA and seminal fluid PSA at two concentration levels were incubated with human female serum at 37° C. for 2 hours. Before and after incubation PSA immunoreactivities were measured by Tosoh AIA ®-600, respectively.

As shown in Table 2, more than 50% of PSA immunoreactivity was lost after seminal fluid PSA was incubated with female serums; only 20% of PSA immunoreactivity was lost after BPH-PSA was incubated with female serum. These results suggest that only 20% of BPH-PSA is enzymatically active, which is confirmed by enzyme assays directly using synthetic substrates S-2586 (for chymotrypsin-like activity) and S-2302 (for trypsin-like activity). As shown in Table 3, in contrast to retaining 95.6% of trypsin-like activity, BPH-PSA lost more than 80% of its chymotrypsin-like activity. The low enzymatic activity of BPH nodule fluid was also confirmed by SDS-PAGE, as shown in Lane 5, FIG. 4, where more than 60% of BPH-PSA was nicked.

TABLE 3

Comparison of enzymatic activities of BPH-PSA and seminal fluid PSA

| substrate | SF-PSA ($A_{405}/hr/A_{280}$) | BPH-PSA ($A_{405}/hr/A_{280}$) |
|---|---|---|
| S-2302 | 4.11 (100%) | 3.93 (95.6%) |
| S-2586 | 33.46 (100%) | 5.76 (16.9%) |

Purified BPH nodule fluid PSA and seminal PSA were incubated with synthetic substrates S-2302 and S-2586 at 37° C. respectively. At the proper time the reactions were terminated by glacial acetic acid. Specific enzyme activity was derived by absorbance at 405 nm per hour of the same amount of protein ($A_{280}$).

Amino-terminal sequence analysis: To identify the fragments of BPH-PSA obtained from gel electrophoresis under reducing and non-reducing conditions, the protein bands from PVDF membrane were subjected to at least ten cycles of amino acid sequence analysis as described in the methods. The results are summarized in Table 4.

TABLE 4

N-Terminal sequences from BPH-PSA

| Sequence Found |  | Residue No. |
|---|---|---|
| (1) I-V-G-G-W-E-C-E-K-H | (SEQ ID NO: 01) | 1–10 |
| (2) V-G-G-W-E-C-E K H S | (SEQ ID NO: 02) | 2–11 |
| (3) H-P-E-D-T-G-Q-V-F-Q | (SEQ ID NO: 03) | 58–67 |
| (4) S-L-F-H-P-E-D-T-G-Q | (SEQ ID NO: 04) | 55–64 |
| (5) K-L-Q-C-V-D-L-H-V-I | (SEQ ID NO: 05) | 146–155 |
| (6) L-Q-C-V-D-L-H-V-I | (SEQ ID NO: 06) | 147–155 |

Sequence analysis demonstrates the existence of a dual amino-terminal sequence of BPH-PSA, starting with IVGGW (SEQ ID NO:07) or VGGW (SEQ ID NO:08). Internal cleavage sites are found between residues His-54 and Ser-55; Phe-57 and His-58; Lys-145 and Lys-146; and Lys-146 and Lys-147.

D. Discussion

The above results demonstrate that BPH-PSA differs from seminal fluid PSA in at least the following three significant ways: 1) most of the BPH nodule fluid PSA has multiple internal cleavage sites leading to a greater loss of enzymatic activity, whereas less than 30% of seminal fluid PSA is "nicked"; 2) BPH nodule fluid PSA has much lower specific chymotrypsin-like activity, although its trypsin-like activity is similar to that in seminal fluid; 3) seminal fluid PSA starts with isoleucine in the N-terminus, whereas the isoleucine in the N-terminus is missing in 50 percent of PSA purified from BPH nodule fluids.

II. PRODUCTION AND CHARACTERIZATION OF MOUSE MONOCLONAL ANTIBODIES TO A FORM(S) OF PROSTATE SPECIFIC ANTIGEN ISOLATED FROM BENIGN PROSTATIC HYPERPLASIA TISSUE (BPH-PSA)

A. Mouse Immunization

BALB/c mice (Jackson Laboratory, Bar Harbor, Me.) were immunized subcutaneously with 50 μg of purified human BPH-PSA in a 1:1 emulsion with complete Freund's adjuvant. Four weeks later, a second subcutaneous immunization of 50 μg BPH-PSA in a 1:1 emulsion with incomplete Freund's adjuvant was given. Two weeks later, the mouse was bled from the tail and the separated serum was tested for the presence of anti-BPH-PSA antibodies by an enzyme-linked immunosorbent assay (ELISA: see below). After determining the presence of anti-BPH-PSA antibodies in these animals, an intraperitoneal injection of 150–200 μg of purified BPH-PSA in physiological saline was given three days before fusion.

B. Cell Fusion

Spleen cells from the immunized mice were fused with the myeloma cell line Sp2/0 (Shulman, M., C. D. Wilde, and G. Kohler (1978) Nature 276, 269) employing the method of Galfre et al. (Galfre, G., S. C. Howe, C. Milstein, G. W. Butcher, and J. C. Howard (1977) Nature 266, 550), as modified by Oi and Herzenberg (Oi, V. T., and L. A. Herzenberg (1980) In B. B. Mishell and S. M. Shiigi (Eds) Selected Methods in Cellular Immunology (W. H. Freeman, San Francisco, Calif.) p. 351), using 50% polyethylene glycol (PEG) 1500 (Boehringer Mannheim, Indianapolis, Ind.). Fused cells were suspended in RPMI-1640 medium (Irvine Scientific, Santa Ana, Calif.) supplemented with 15% fetal bovine serum (Hyclone Labs, Logan, Utah), gentamycin, Fungizone, and a preformulated hypoxanthene-aminopterin-thymidine mixture (HAT medium supplement. Sigma Chemical Co., St. Louis, Mo.). Suspended cells were then distributed into 96-well cell culture plates at 0.2 million spleen cells/0.1 mL medium/well. Cell culture wells had been previously seeded with 0.1 mL each of a suspension of mouse peritoneal exudate macrophages in the above described culture medium (HAT medium) at 50,000 macrophages/mL of medium. Cell cultures were fed with fresh HAT medium for 4–5 days. When the wells were 20–50% confluent with hybridoma cell growth (10–14 days), culture medium was collected from the wells and screened for anti-BPH-PSA antibody by an ELISA (see below).

C. Screening ELISA

ELISA was used for screening assays. Briefly, wells of 96-well polystyrene microtiter plates were coated with 100 μL of 100 ng/mL BPH-PSA antigen for 2 hours at room temperature in 0.01M phosphate buffered saline (PBS) containing 0.10% sodium azide. Wells were also tested with human seminal plasma derived PSA, purified by the method of Sensabaugh & Blake (Sensabaugh, G. F. and E. T. Blake (1990) J. Urology 144, 1523) and PSA-ACT complex which was prepared according to the method of Chen et al. (Chen, Z., A. Prestigiacomo, and T. A. Stamey (1995) Clin. Chem. 41 (9), 1273). Wells were then washed three times with PBS containing 0.05% Tween 20 (PBS-T). Cell culture supernatants were added to the wells after diluting 1:2 in PBS-T containing 0.5% gelatin and 1% bovine serum albumin. The plates were incubated for 1 hour at room temperature. Wells were washed as described above and then horseradish peroxidase-labeled goat anti-mouse IgG (Fc specific) (Jackson Immunoresearch Labs., West Grove, Pa.), at appropriate concentration in assay dilution buffer, was added to the wells and the plate was incubated for 30 minutes at room temperature. After washing as described above, a color development solution (o-phenylenediamine hydrogen peroxide, Diagnostic Products Corporation, Los Angeles, Calif.) was added to the wells. After 15–20 minutes at room temperature, color development was terminated by addition of 1N sulfuric acid. Absorbance was determined at 490 nm using a microplate EIA reader (Milenia Kinetic analyzer).

D. Cloning

The hybridoma cell cultures identified as secreting antibodies specific to only BPH-PSA were subsequently cloned at least two to three times by the limiting dilution procedure (Oi, V. T., and L. A. Herzenberg (1980) In B. B. Mishell and S. M. Shiigi (Eds) Selected Methods in Cellular Immunology (W. H. Freeman, San Francisco, Calif.) p. 351), using the above described ELISA for screening cloning plates. The antibody designations are 3F12, 3H1, 3H4, 5F3, 6C5, 7D1, 7E8, 1C7, 4B5, 4C4, 5B5, 7E12 and 7H9. Hybridoma cell lines secreting these antibodies are deposited and maintained under the control of Stanford University and can be obtained by the Patent Office by contacting Thomas A. Stamey, a coinventor of the present application. Furthermore, hybridomas secreting 3F12, 3H1, 3H4, 5F3, 6C5, 7D1, 7E8, 1C7, 4B5, 4C4, 5B5, 7E12 and 7H9 have been deposited with the ATCC and give ATCC accession nos. HB-12483, respectively.

It is evident from the above results and discussion that the subject invention provides for improved methods of diagnosing prostate cancer because of its potential for estimating the amount of serum PSA contributed by non-cancerous BPH tissue. By providing for BPH-PSA specific antibodies, the subject invention provides for the specific identification of BPH in a patient, whereby elevated serum PSA levels can then more reliably be assigned to the presence of BPH or prostate cancer, leading to improved prostate cancer screening results. Moreover, since there is no acceptable definition of BPH in men with non-cancerous, obstructive prostatic symptoms, this invention also offers an objective, serum estimate of the amount of BPH which could be a valuable adjunct in treating and evaluating therapeutic responses to reducing the amount of BPH tissue in the prostate.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of obtaining a preparation of Benign Prostatic Hyperplasia Prostate Specific Antigen (BPH-PSA), the method comprising:
   obtaining a fluid comprising BPH-PSA from BPH nodules; and
   enriching the fluid with respect to said BPH-PSA.

2. The method according to claim 1, wherein the obtaining step comprises:
   harvesting BPH nodules from a human male patient having benign prostatic hyperplasia;
   piercing the nodules to release fluid present in said nodules, whereby BPH nodule fluid is released from the nodules; and
   collecting the released BPH-nodule fluid that comprises BPH-PSA.

3. The method according to claim 2, wherein the enriching step comprises subjecting the fluid comprising BPH-PSA to at least one protein purification procedure.

4. The method according to claim 3, wherein the at least one protein purification procedure is a chromatographic procedure.

5. The method according to claim 4, wherein the chromatographic procedure is selected from the group consisting of gel chromatography and ion-exchange chromatography.

6. A method for purifying BPH-PSA from a naturally occurring fluid comprising BPH-PSA, the method comprising:
   harvesting BPH nodules from a human male patient having benign prostatic hyperplasia;
   piercing the nodules to release BPH nodule fluid present in the nodules;
   collecting the released BPH-nodule fluid;
   subjecting the BPH-nodule fluid to a two step purification procedure comprising gel chromatography and ion-exchange chromatography;
   whereby the BPH-PSA is purified.

7. The method according to claim 6, wherein said purified BPH-PSA is subjected to gel electrophoresis.

8. BPH-PSA having an enzymatic activity that differs from seminal fluid PSA.

9. The BPH-PSA according to claim 8, wherein the BPH-PSA is present in substantially pure form.

10. The BPH-PSA according to claim 8, wherein the BPH-PSA is present in a preparation at least partially purified with respect to the BPH-PSA.

11. The BPH-PSA of claim 8, wherein the BPH-PSA comprises substantially the same trypsin like activity but substantially reduced chymotrypsin like activity as compared to seminal fluid PSA.

12. The BPH-PSA of claim 8, wherein the BPH-PSA migrates as a single band of 30 kDa molecular weight on SDS-PAGE under non-reducing conditions.

13. The BPH-PSA of claim 8 having an N-terminal sequence of VGGW.

14. A composition comprising at least about 90% by wt BPH-PSA according to claim 8.

15. An antibody that specifically reacts with BPH-PSA according to claim 8.

16. The antibody of claim 15, wherein the antibody is a polyclonal antibody.

17. The antibody of claim 15, wherein the antibody is a monoclonal antibody.

18. A method for detecting the presence of BPH-PSA according to claim 8 in a sample, the method comprising:

contacting a sample suspected of comprising BPH-PSA with antibody specific for BPH-PSA, whereby BPH-PSA binds to the antibody to produce antibody binding complexes;

detecting the presence of the antibody binding complexes;

relating the presence of the antibody binding complexes to the presence of BPH-PSA in the sample.

19. The method according to claim 18, wherein the method further comprises contacting the antibody binding complexes with a second labeled antibody specific for the antibody binding complexes and the detecting comprises detecting the second labeled antibody.

20. An immunoassay device for use in the detection of BPH-PSA in a sample, said device comprising a measuring region having an antibody according to claim 15 bound to it.

21. A hybridoma capable of secreting the antibody according to claim 17.

* * * * *